United States Patent
Okoba et al.

(10) Patent No.: US 10,473,633 B2
(45) Date of Patent: Nov. 12, 2019

(54) PREPARATIVE SEPARATION CHROMATOGRAPH

(71) Applicant: SHIMADZU CORPORATION, Kyoto-shi, Kyoto (JP)

(72) Inventors: Tsutomu Okoba, Kyoto (JP); Takayuki Iriki, Fulton, MD (US)

(73) Assignee: SHIMADZU CORPORATION, Kyoto-shi, Kyoto (JP)

(*) Notice: Subject to any disclaimer, the term of this patent is extended or adjusted under 35 U.S.C. 154(b) by 471 days.

(21) Appl. No.: 15/088,280

(22) Filed: Apr. 1, 2016

(65) Prior Publication Data
US 2016/0290976 A1 Oct. 6, 2016

(30) Foreign Application Priority Data
Apr. 3, 2015 (JP) .................. 2015-076422

(51) Int. Cl.
*B01D 15/24* (2006.01)
*G01N 30/80* (2006.01)
(Continued)

(52) U.S. Cl.
CPC ............ *G01N 30/80* (2013.01); *B01D 15/24* (2013.01); *B01D 15/247* (2013.01); *G01N 30/82* (2013.01);
(Continued)

(58) Field of Classification Search
CPC ...... B01D 15/22; B01D 15/24; B01D 15/247; G01N 30/82; G01N 30/88; G01N 30/8665;
(Continued)

(56) References Cited

U.S. PATENT DOCUMENTS 6,737,022 B1 * 5/2004 Sutton .................. B01D 15/247
222/630

FOREIGN PATENT DOCUMENTS

JP  03108660 A   5/1991
JP  05092717 U  12/1993
(Continued)

OTHER PUBLICATIONS

Dionex, "Chromeleon Chromatography Management System: Tutorial and User Manual", Apr. 2005.*
(Continued)

*Primary Examiner* — Benjamin L Lebron
(74) *Attorney, Agent, or Firm* — Sughrue Mion, PLLC

(57) ABSTRACT

Provided is a preparative separation chromatograph including: a chromatograph 10 having a detector 15; a fraction collector 20; a controller 34 for commanding the fraction collector to initiate a component-collecting operation with reference to a point when the rate of change in an output signal from the detector 15 exceeds a positive reference value and to discontinue the operation with reference to a point when the absolute value of the rate of change becomes smaller than that of a negative reference value after the rate of change turns negative; a storage section 31 for storing sampling-rate information which relates the value of the output signal to the time interval at which the controller determines the rate of change; and a sampling rate determiner 33 for determining the time interval for calculating the rate of change based on the sampling-rate information and actual values of the output signal.

2 Claims, 2 Drawing Sheets

(51) Int. Cl.
*G01N 30/82* (2006.01)
*G01N 30/86* (2006.01)
*G01N 30/88* (2006.01)
*G01N 30/34* (2006.01)

(52) U.S. Cl.
CPC ......... *G01N 30/86* (2013.01); *G01N 30/8624* (2013.01); *G01N 30/8651* (2013.01); *G01N 30/8658* (2013.01); *G01N 30/88* (2013.01); *G01N 30/34* (2013.01); *G01N 30/8696* (2013.01)

(58) Field of Classification Search
CPC ........ G01N 30/34; G01N 30/80; G01N 30/86; G01N 30/8624; G01N 30/8651; G01N 30/8658; G01N 30/8696
See application file for complete search history.

(56) References Cited

FOREIGN PATENT DOCUMENTS

| | | |
|---|---|---|
| JP | 2000-214151 A | 8/2000 |
| JP | 2005055262 A | 3/2005 |
| JP | 2007-183173 A | 7/2007 |

OTHER PUBLICATIONS

Dyson, N., "Peak distortion, data sampling errors and the integrator in the measurement of very narrow chromatographic peaks", Journal of Chromatography A, 842, pp. 321-340 (1999).*
Khan, M., et al., "Numerical integration schemes for unequal data spacing", American Journal for Applied Mathematics, 5(2), pp. 48-56 (2017).*
Blake, L., "A modified simpson's rule and fortran subroutine for cumulative numerical integration of a function defined by data points", Naval Research Laboratory Memorandum Report 2231, Apr. 1971. Available online Aug. 19, 2014.*

\* cited by examiner

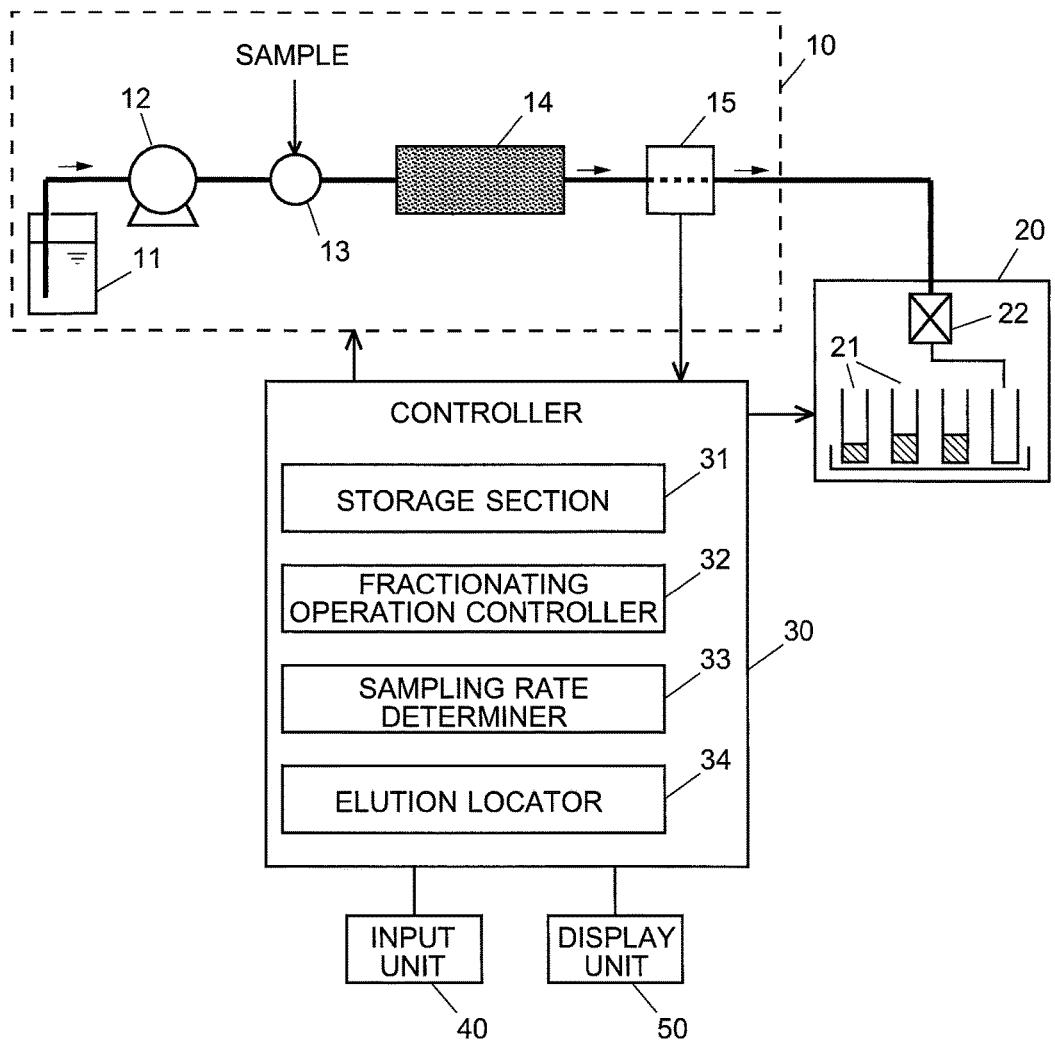

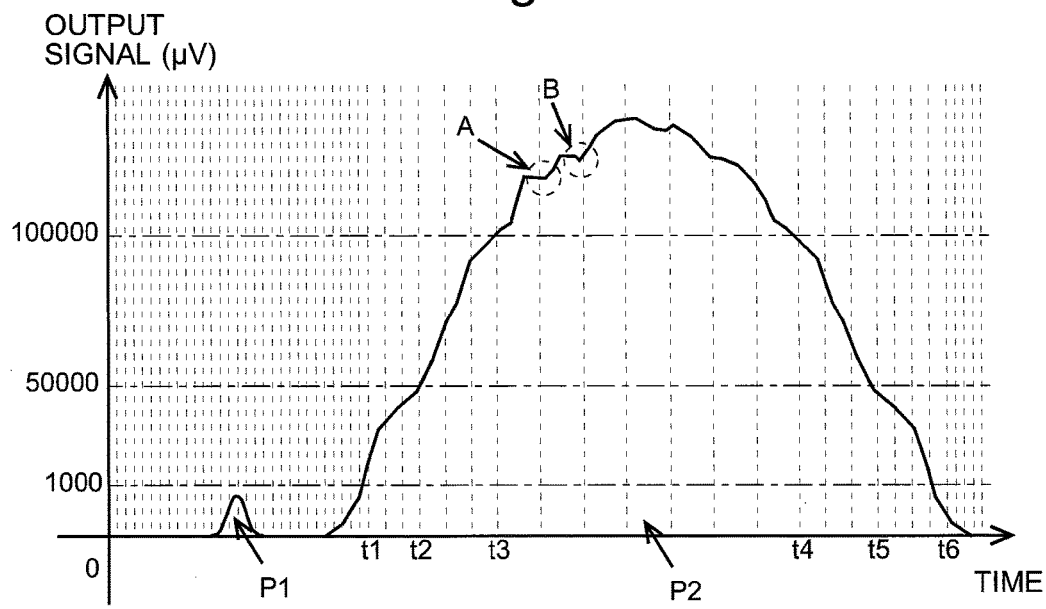

PREPARATIVE SEPARATION CHROMATOGRAPH

TECHNICAL FIELD

The present invention relates to a preparative separation chromatograph in which the target components separated by a column in a chromatograph are individually collected with a fraction collector.

BACKGROUND ART

As a system for separating the components contained in a sample and individually collecting those components, a preparative separation chromatograph is commonly known, in which the components are temporally separated by a column in a high-performance liquid chromatograph or similar apparatus, and each component is subsequently collected with a fraction collector (for example, see Patent Literatures 1 and 2).

The preparative separation chromatograph includes a separation unit having a liquid-sending pump and a column, a detector located behind the separation unit, a fraction collector, as well as a controller for controlling those devices. The sample components which have been eluted from the column in a temporally separated form are sequentially detected by the detector (e.g. an ultraviolet visible spectrophotometer) and introduced into the fraction collector in the subsequent stage. In the fraction collector, the internal passage is switched according to the command from the controller so that the target components are respectively collected into fraction containers, such as vials.

Many preparative separation chromatographs are capable of so-called "automatic fractionation", i.e. the automatic collection of the components eluted from the column. In automatic fractionation, the controller locates the beginning and ending points of the elution of each component based on the output signal from the detector. It controls the fraction collector so as to initiate the collecting operation after a predetermined amount of time from the beginning of the elution of one component and discontinue the operation after the predetermined amount of time from the end of the elution of the component. The "predetermined amount of time" corresponds to the amount of time required for a component which has passed through the detector to reach the collecting section of the fraction collector, which is determined by the length of the passage from the detector to the fraction collector, the flow velocity of the mobile phase, and other factors.

Automatic fractionation is roughly divided into two types: the "level method", which uses a threshold, and the "slope method", which uses a rate of change. In the level method, the point in time where the output signal from the detector exceeds a threshold is located as the beginning point of a chromatogram peak (the beginning of the elution of a component), while the point in time where the signal falls below the threshold is located as the ending point of the peak (the end of the elution of the component). However, as in the case of the gradient elution method in which the composition of the mobile phase is changed with time, if the background level of the chromatogram changes with time, it is difficult to correctly locate the beginning and ending points of the elution of the component by the level method. Furthermore, locating those points will be totally impossible if the background level exceeds the threshold.

In the slope method, the output signal from the detector is acquired at predetermined time intervals, and the rate of change from the previously acquired output signal is calculated. The point in time where the magnitude of the rate of change becomes greater than a positive predetermined slope value is located as the beginning point of a chromatogram peak (i.e. the beginning of the elution of a component), while the point in time where the absolute value of the rate of change becomes smaller than an absolute value of a negative predetermined slope value is located as the ending point of the chromatogram peak (i.e. the end of the elution of the component). For example, if the positive slope value is 200 μV/sec and the negative slope value is −200 μV/sec, the point in time where the slope of the change in the signal intensity of the detector exceeds 200 μV/sec is located as the beginning point of the peak. After passing the peak top, the rate of change in the signal intensity turns negative. Subsequently, the point in time where the absolute value of the rate of change becomes smaller than the absolute value (200 μV/sec) of the negative slope value is located as the ending point of the peak. In this manner, according to the slope method, the beginning and ending points of the peak are located by examining the rate of change in the output signal, and not the absolute value of the signal. This method can be used even when the background level changes with time.

CITATION LIST

Patent Literature

Patent Literature 1: JP 2000-214151 A
Patent Literature 2: JP 2007-183173 A

SUMMARY OF INVENTION

Technical Problem

In the previously described preparative separation chromatograph, the controller acquires the output signal from the detector at predetermined time intervals. The time interval is set so that it will be approximately equal to one tenth of the full width at half maximum of the peak which occurs when a component of an average content is detected (standard peak), i.e. so that one peak will be represented by approximately 20 measurement points. This is because setting too small a number of measurement points for one peak deteriorates the reproducibility of the peak, while setting too large a number of measurement points requires the smoothing of the peak data to moderate the influence of the variation among the measurement points.

However, the amounts of various components actually contained in a sample are not uniform. That is to say, a peak formed on a mass chromatogram by a low-quantity component is narrower and lower than the standard peak, while a peak formed by a high-quantity component is broader and higher than the standard peak. As already described, the conventional preparative separation chromatograph acquires output signals from the detector at predetermined time intervals regardless of the quantity of the component and performs the process for locating the beginning and ending points of the elution of the component. Therefore, a low peak formed by a low-quantity component may be missed, allowing the component to avoid the collection process, or conversely, a fluctuation of the detection signal on a peak formed by a high-quantity component may be mistaken for the end of the peak, causing the collection of the component to be incorrectly discontinued.

The problem to be solved by the present invention is to provide a preparative separation chromatograph capable of accurately locating the beginning and ending points of the elution of a component contained in a sample and collecting the same component, regardless of the quantity of the compound.

Solution to Problem

The preparative separation chromatograph according to the present invention developed for solving the previously described problem includes:

a) a chromatograph having a column for temporally separating one or a plurality of target components contained in a sample and a detector for detecting each target component eluted from the column;

b) a fraction collector for collecting a target component exiting from the detector;

c) a controller for determining the rate of change in an output signal from the detector based on the output signal, for commanding the fraction collector to initiate a collecting operation for the target component with reference to a point in time where the rate of change becomes greater than a positive predetermined reference value, and for commanding the fraction collector to discontinue the collecting operation for the target component with reference to a point in time where the absolute value of the rate of change becomes smaller than the absolute value of a negative predetermined reference value after the rate of change turns negative;

d) a storage section for storing sampling-rate information in which the value of the output signal from the detector is related to the time interval at which the controller determines the rate of change in the output signal; and e) a sampling rate determiner for determining the time interval at which the controller determines the rate of change in the output signal, based on the sampling-rate information and the value of the output signal acquired from the detector by the controller.

One example of the sampling-rate information is a table in which the dynamic range of the detector is divided into segments, with each segment being related to one value of the time interval. Another example is a mathematical formula for calculating the time interval from the value of the output signal from the detector.

The operation of "commanding the fraction collector to initiate a collecting operation for the target component with reference to a point in time where the rate of change becomes greater than a positive predetermined reference value" means commanding the fraction collector to initiate the collecting operation for a target component at a point in time which is delayed by a predetermined amount of time from the point in time where the rate of change has become greater than the positive predetermined reference value (the beginning point of the elution of the target component). The "predetermined amount of time" corresponds to the amount of time required for a component which has passed through the detector to reach the collecting section of the fraction collector (delay time), which is determined by the length of the passage from the detector to the fraction collector, the moving speed of the target component (the flow velocity of the mobile phase), and other factors. The discontinuation of the collecting operation for the target component is also similarly performed: The fraction collector is commanded to discontinue the collecting operation for the target component at a point in time which is delayed by the predetermined amount of time from the point in time where the absolute value of the rate of change has become smaller than the absolute value of the negative predetermined reference value (i.e. the ending point of the elution of the target component) after the rate of change has turned negative.

The time interval at which the controller acquires the output signal from the detector only needs to be equal to or shorter than the time interval at which the controller determines the rate of change in the output signal; the two intervals do not always need to be equal to each other. For example, the controller may be configured so as to acquire the output signal from the detector at predetermined time intervals equal to or less than the shortest possible interval of time for determining the rate of change, and to use only a portion of the acquired output signals to determine the rate of change in the output signal.

A peak formed by a low-quantity component is narrower and lower than the standard peak, while a peak formed by a high-quantity component is broader and higher than the standard peak. In order to deal with such a variation in the width and height of the peak depending on the quantity of the component, the sampling-rate information is prepared so that a shorter interval of time for determining the rate of change will be set for lower levels of output signal from the detector, while a longer interval of time for determining the rate of change will be set for higher levels of output signal. This setting prevents the situation in which a low peak formed by a low-quantity component is missed, allowing the component to avoid the collection process, as well as the situation in which a fluctuation of the detection signal on a peak formed by a high-quantity component is mistaken for the end of the peak. Therefore, regardless of the quantity of the component in the sample, the beginning and ending points of the elution of the target component can be accurately located, and the component can be collected with the fraction collector.

Another aspect of the present invention developed for solving the previously described problem is a method for collecting a target component using a preparative separation chromatograph configured to initiate a collecting operation for the target component with reference to a point in time where the rate of change in a detection signal of one or a plurality of target components temporally separated by a column in a chromatograph becomes greater than a positive predetermined reference value and to discontinue the collecting operation for the target component with reference to a point in time where the absolute value of the rate of change becomes smaller than the absolute value of a negative predetermined reference value after the rate of change turns negative, wherein:

the rate of change in the detection signal is determined at time intervals depending on the magnitude of the value of the detection signal.

Advantageous Effects of the Invention

By using the preparative separation chromatograph or the method for collecting a target component according to the present invention, the beginning and ending points of the elution of the target component can be accurately located, and the component can be collected with the fraction collector, regardless of the quantity of the component in the sample.

BRIEF DESCRIPTION OF DRAWINGS

FIG. 1 is a configuration diagram showing the main components of one embodiment of the preparative separation chromatograph according to the present invention.

FIG. 2 is one example of the sampling-rate information used in the preparative separation chromatograph of the present embodiment.

FIG. 3 is a graph showing a chromatogram created in the present embodiment and the time intervals at which the rate of change in the output signal is calculated.

DESCRIPTION OF EMBODIMENTS

A preparative separation liquid chromatograph as one embodiment of the preparative separation chromatograph according to the present invention as well as a method for collecting target components using the same preparative separation liquid chromatograph are hereinafter described with reference to the drawings.

FIG. 1 shows the configuration of the main components of the preparative separation liquid chromatograph of the present embodiment. The preparative separation liquid chromatograph of the present embodiment includes a liquid chromatograph unit 10 for separating target components contained in a sample, a fraction collector 20 for collecting the target components separated by the liquid chromatograph unit 10, and a controller 30 for controlling the operations of these units.

In the liquid chromatograph unit 10, a mobile phase held in a mobile phase container 11 is suctioned by a liquid-sending pump 12 and supplied to a column 14 at a predetermined flow rate. A sample which contains target components is injected through a sample injector 13 and transported into the column 14 by the flow of the mobile phase. The target components in the sample are temporally separated within the column 14 and eluted. The target components eluted from the column 14 are detected by an ultraviolet visible spectrophotometer 15 and introduced into the fraction collector 20. The ultraviolet visible spectrophotometer 15 detects the target components at a detection cycle of 100 Hz. The detection signals are stored in a storage section 31 (which will be described later).

The fraction collector 20 includes a plurality of fraction containers 21 and a solenoid valve 22 which functions as the passage-switching unit. The solenoid valve 22 operates according to the control signal from a fractionating operation controller 32 (which will be described later) so as to connect the passage from the liquid chromatograph unit 10 to one of the fraction containers 21 or the drain.

The controller 30 includes a fractionating operation controller 32, sampling rate determiner 33 and elution locator 34 as the functional blocks in addition to the storage section 31. The controller 30 is actually a personal computer on which necessary software programs are installed. An input unit 40 and display unit 50 are connected to the personal computer. The storage section 31 holds the slope values (±200 μV/sec) used by the elution locator 34 in locating the beginning and ending points of the elution of the target component, as well as the sampling-rate information.

The sampling-rate information is the information which relates the values (thresholds) of the output signal from the ultraviolet visible spectrophotometer 15 to the time interval at which the elution locator 34 calculates the rate of change in the output signal. In the present embodiment, the information in a table format as shown in FIG. 2 is used. The following relations are defined: a sampling rate of 100 Hz for output signals of 1000 μV or less, a sampling rate of 50 Hz for output signals of 1000 μV or higher and less than 50000 μV, a sampling rate of 20 Hz for output signals of 50000 μV or higher and less than 100000 μV, as well as a sampling rate of 5 Hz for output signals of 100000 μV or higher. Other than the table format, a mathematical formula for calculating the sampling rate from the value of the output signal can also be used as the sampling-rate information.

The collecting operation of the target component in the preparative separation chromatograph of the present embodiment is hereinafter described.

Upon receiving a command to initiate the preparative separation from the user, the fractionating operation controller 32 reads the positive and negative slope values (±200 μV/sec) as well as the sampling-rate information stored in the storage section 31, and displays them on the display unit 50. After appropriately editing the slope values and the sampling-rate information using the input unit 40, the user performs the fixing operation, whereby the edited data are fixed as the slope values and the sampling-rate information to be used in the process of collecting target components in a real sample.

The fractionating operation controller 32 commands the components of the liquid chromatograph 10 and those of the fraction collector 20 to initiate their operations ("fractionating operation"). It also calculates the delay time td based on the flow velocity of the mobile phase in the fractionating operation, the length of the passage from the ultraviolet visible spectrophotometer 15 to the solenoid valve 22 in the fraction collector 20, and other factors. The delay time td is the amount of time required for a target component which has passed through the ultraviolet visible spectrophotometer 15 to reach the solenoid valve 22 which is the collecting section of the fraction collector 20.

After the fractionating operation for the target component is initiated, the fractionating operation controller 32 determines a correction value so that the value of the detection signal initially produced by the ultraviolet visible spectrophotometer 15 becomes the zero point (0 μV) of the output signal of the ultraviolet visible spectrophotometer 15. This correction value is applied to all of the subsequent output signals. Additionally, the fractionating operation controller 32 creates a chromatogram based on the (corrected) output signals from the ultraviolet visible spectrophotometer 15 and displays it on the display unit 50. FIG. 3 shows one example of the chromatogram created in the present embodiment.

Since the output signal at the beginning of the fractionating operation is 0 μV, the sampling rate determiner 33 sets the sampling rate at 100 Hz according to the sampling-rate information. The elution locator 34 determines the rate of change in the output signal at this sampling rate (100 Hz). For every acquisition of the output signal at 100 Hz, the elution locator 34 calculates the rate of change in the output signal and determines whether or not the rate has exceeded the positive slope value (200 μV/sec). The point in time (ta) where the rate has exceeded the slope value is located as the beginning point of the elution of the target component. After the beginning point of the elution of the target component is located by the elution locator 34, the fractionating operation controller 32 operates the solenoid valve 22 of the fraction collector 20 at the point in time (ta+td) delayed from time ta by delay time td so as to collect the target component in one of the fraction containers 21.

The sampling rate determiner 33 further continues the monitoring of the output signal from the ultraviolet visible spectrophotometer 15. At a point in time (t1) where the value of the output signal has reached or exceeded the lowest threshold (1000 μV) specified in the sampling-rate information, the sampling rate determiner 33 changes the sampling rate to 50 Hz. Simultaneously, the elution locator 34 changes the time interval for determining the rate of change in the output signal to 50 Hz. After that, the sampling rate determiner 33 changes the sampling rate to 20 Hz at a point in time (t2) where the value of the output signal has reached 50000 μV or higher, and further to 5 Hz at a point in time (t3) where the value of the output signal has reached 100000 μV or higher.

After the beginning of the elution of the target component, when the peak top of the mass chromatogram is passed, the amount of elution of the target component begins to gradually decrease, and the rate of change in the value of the output signal from the ultraviolet visible spectrophotometer 15 turns negative. After that, the sampling rate determiner 33 changes the sampling rate to 20 Hz at a point in time (t4) where the value of the output signal has fallen below the threshold (100000 μV) specified in the sampling-rate information, to 50 Hz at a point in time (t5) where the value of the output signal has fallen below 50000 μV, and to 100 Hz at a point in time (t6) where the value of the output signal has fallen below 1000 μV.

Meanwhile, the elution locator 34 locates, as the ending point of the elution of the target component, the point in time tb where the absolute value of the rate of change in the value of the output signal falls below the absolute value (200 μV/sec) of the negative slope value. After the ending point of the elution of the target component is located by the elution locator 34, the fractionating operation controller 32 operates the solenoid valve 22 of the fraction collector at the point in time (tb+td) delayed from time tb by delay time td to discontinue the collection of the target component.

In the present embodiment, as shown in FIG. 3, the time interval at which the rate of change in the output signal is determined is shortened within a period of time where the output signal has small values. Therefore, the micro-sized peak P1 corresponding to a low-quantity component will not be missed, and the component will be assuredly collected. Conversely, the time interval at which the rate of change in the output signal is determined is elongated within a period of time where the output signal has large values. Therefore, a minor fluctuation of the output signals forming the macro-sized peak P2 corresponding to a high-quantity component (e.g. the fluctuation of the output signal at point A or B on peak P2 in FIG. 3) will not be mistaken for the end of the elution of the component, and the component will be accurately collected.

The previous embodiment is a mere example and can be appropriately changed within the spirit of the present invention. For example, in the previous embodiment, the influence of the background is reduced by the correction in which the output signal initially acquired from the detector is set as the zero value. As in the case of the gradient elution method, if the background changes with time, the influence of the background can be reduced as follows:

Initially, before the preparative separation of the target components in the sample, the mobile phase is solely supplied (with no sample injection) and detected under the same gradient condition as in the preparative separation of the target components. The thereby acquired output signals from the detector ("blank data") are stored in the storage section 31. Next, when the preparative separation of the target components in a real sample is performed, the blank data are subtracted from the output signals before the rate of change in the output signal is calculated to locate the beginning and ending points of the elution of the target component. By this operation, the influence of the background which occurs in the case of using the gradient elution method is eliminated, so that the target components can be accurately collected.

Alternatively, it is also possible to acquire both the detection signals under a condition for detecting both the target components and the mobile phase in the detector and the detection signals under a condition for detecting only the mobile phase, and to subtract the latter detection signals from the former ones. According to this method, since the blank data used for the subtraction is acquired in real time, the influence of a change in the background caused by a change in the environment around the preparative separation chromatograph (e.g. a temperature change) can also be removed. If the detector is an ultraviolet visible spectrophotometer, the blank data can be obtained by performing an absorbance measurement using a wavelength at which an absorption of light by the mobile phase occurs while no absorption by the target components occurs. If the detector is a mass spectrometer, the blank data can be obtained by performing a selective ion monitoring measurement at a mass-to-charge ratio at which an ion is generated from the mobile phase while no generation of ions from the target components occurs.

REFERENCE SIGNS LIST

10 . . . Liquid Chromatograph
11 . . . Mobile Phase Container
12 . . . Liquid-Sending Pump
13 . . . Sample Injector
14 . . . Column
15 . . . Ultraviolet Visible Spectrophotometer
20 . . . Fraction Collector
21 . . . Fraction Container
22 . . . Solenoid Valve
30 . . . Controller
31 . . . Storage Section
32 . . . Fractionating Operation Controller
33 . . . Sampling Rate Determiner
34 . . . Elution Locator
40 . . . Input Unit
50 . . . Display Unit

The invention claimed is:
1. A preparative separation chromatograph system, comprising:
   a) a chromatograph having a column configured to temporally separate one or a plurality of target components contained in a sample and a detector configured to detect each target component eluted from the column;
   b) a fraction collector configured to collect a target component exiting from the detector;
   c) a controller configured to execute controller-executable instructions to:
      store, in a storage section, sampling-rate information which relates a plurality of threshold values of an output signal from the detector to a plurality of sampling rates, the sampling-rate information being prepared so that a higher sampling rate is set for lower levels of the output signal, while a lower sampling rate is set for higher levels of the output signal;
      acquire a value of the output signal from the detector;
      determine a sampling rate corresponding to the acquired value of the output signal with reference to the stored sampling-rate information;
      determine a rate of change in the output signal in the determined sampling rate;
      command the fraction collector to initiate a collecting operation for the target component with reference to a point in time where the rate of change becomes greater than a positive predetermined reference value; and command the fraction collector to discontinue the collecting operation for the target component with reference to a point in time where an absolute value of the rate of change becomes smaller than an absolute value of a negative predetermined reference value after the rate of change turns negative.

2. A method for collecting a target component using a preparative separation chromatograph, the method comprising:

storing sampling-rate information which relates a plurality of threshold values of an output signal from a detector to a plurality of sampling rates, the sampling-rate information being prepared so that a higher sampling rate is set for lower levels of the output signal, while a lower sampling rate is set for higher levels of the output signal;

acquiring a value of the output signal from the detector;

determining a sampling rate corresponding to the acquired value of the output signal with reference to the stored sampling-rate information;

determining a rate of change in the output signal in the determined sampling rate;

initiating a collecting operation for a target component with reference to a point in time where the rate of change in a detection signal of one or a plurality of target components temporally separated by a column in a chromatograph becomes greater than a positive predetermined reference value; and discontinuing the collecting operation for the target component with reference to a point in time where an absolute value of the rate of change becomes smaller than an absolute value of a negative predetermined reference value after the rate of change turns negative.

* * * * *